United States Patent [19]

Herrinton

[11] Patent Number: 5,405,978

[45] Date of Patent: Apr. 11, 1995

[54] OXIDATIVE PREPARATION OF 3,5-SECOANDROST-5-ONE-3,17 β-DIOIC ACID

[75] Inventor: Paul M. Herrinton, Kalamazoo, Mich.

[73] Assignee: The Upjohn Company, Kalamazoo, Mich.

[21] Appl. No.: 158,174

[22] Filed: Nov. 24, 1993

Related U.S. Application Data

[63] Continuation of Ser. No. 761,734, filed as PCT/US90/02622, May 15, 1990, abandoned, which is a continuation-in-part of Ser. No. 462,417, Jan. 9, 1990, abandoned, which is a continuation-in-part of Ser. No. 358,800, May 30, 1989, abandoned.

[51] Int. Cl.$^6$ .................. C07D 303/31; C07C 61/135
[52] U.S. Cl. ...................................... 549/544; 562/499
[58] Field of Search ................ 549/532, 544; 562/499; 546/77

[56] References Cited

U.S. PATENT DOCUMENTS

| | | | |
|---|---|---|---|
| 2,727,905 | 12/1955 | Nathan et al. | 562/499 |
| 3,285,918 | 11/1966 | Doorenbos et al. | 544/245 |
| 4,220,775 | 9/1980 | Rasmussen et al. | 546/77 |
| 4,325,878 | 4/1982 | McCombs | 260/397.1 |

FOREIGN PATENT DOCUMENTS

| | | | |
|---|---|---|---|
| 0277002 | 8/1988 | European Pat. Off. | |
| 1510055 | 1/1968 | France | 562/499 |

OTHER PUBLICATIONS

Rasmussen et al., J. Med. Chem., 27, pp. 1690–1701 1984.
Dauben et al., J. Org. Chem. pp. 1787–1788 1958.
Oliveto, et al. JACS, vol. 78, 1956 pp. 1414 to 1416.
Piatak, et al. J. Org. Chem. 1968 pp. 112–116.
Rasmusson, et al. J. Med. Chem. 29CID 1987 2298–2315.
David M. Piatak, et al. "Oxidation of Steroidal Ketones. VII. Cleavage of Sterodial Conjugated Ketones With Ruthenium Tetroxide", The Journal of Organic Chemistry vol. 34, No. 1, Jan. 1969.
Eugene P. Oliveto, et al. "11-Oxygenated Steroids. (List continued on next page.)

*Primary Examiner*—Mukund J. Shah
*Assistant Examiner*—Pavanaram K. Sripada
*Attorney, Agent, or Firm*—Bruce Stein

[57] ABSTRACT

The present invention is an oxidative process for the conversion of 21-unsaturated progesterones (I)

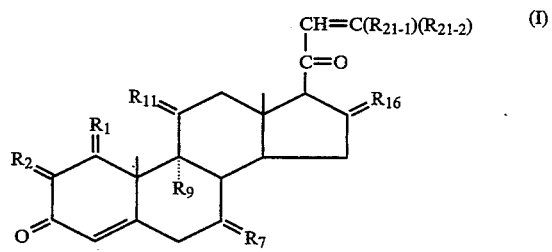

to the corresponding 3,5-secoandrost-5-one-3,17β-dioic acids (II)

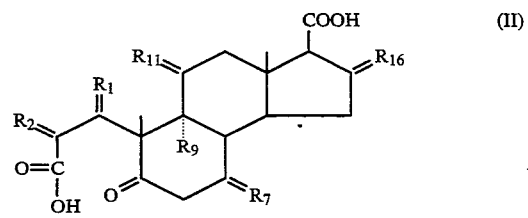

by use of either ozone or an oxidizing agent, which are useful intermediates in the production of Δ$^5$-4-aza-17-carbonyl steroids (III) which are useful in production of 5α-4-aza amide (IV) pharmaceuticals. Also disclosed are the novel 21-unsaturated progesterones (I-C) and 3,5-secoandrost-5-one-3,17β-dioic acids (II-C).

11 Claims, No Drawings

OTHER PUBLICATIONS

XIV. New Syntheses Of Corticosterone", Journal of the American Chemical Society, vol. 78, No. 7, Apr. 5, 1959.

G. R. Allen, Jr., and M. J. Weiss, The Base-catalyzed Condensation of Progesterone with Ehtyl Oxalate, J.A.C.S., 82:1709–1714 (5 Apr. 1960).

W. G. Dauben et al., An Ozonide of Cholestenone, J.O.C., 23:1787–1788 (Nov. 1958).

G. H. Rasmusson et al., Azasteroids as Inhibitors of Rat Prostatic 5α-Reductase, J. Med. Chem., 27:1690–1701 (1984).

E. P. Oliveto et al., 11-Oxygenated Steroids. XIV. New Syntheses of Corticosterone, J.A.C.A., 78:1414–1416 (5 Apr. 1956).

D. Yang and S. W. Pelletier, Ozonolysis of Hydroxymethylene Ketones: The Baeyer-Villiger Reaction as a Source of Anhydride Formation, Chem. Comm., 1055–1057 (1968).

OXIDATIVE PREPARATION OF 3,5-SECOANDROST-5-ONE-3,17 β-DIOIC ACID

The present patent application is a continuation application of U.S. patent application Ser. No. 07/761,734, filed 6, Sept. 1991 abandoned, which is a continuation (national phase) application of international patent application PCT/US90/02622 filed May 15, 1990, which is a continuation-in-part of U.S. application Ser. No. 07/462,417, filed Jan. 9, 1990, abandoned, which is a continuation-in-part of U.S. application Ser. No. 07/358,800, filed May 30, 1989, abandoned.

BACKGROUND OF THE INVENTION

1. Field of the Invention

The present invention is an oxidative process for the conversion of 21-unsaturated progesterones to the corresponding 3,5-secoandrost-5-one-3,17β-dioic acid.

2. Description of the Related Art

The 21-unsaturated progesterones (I) are known compounds, see J.A.C.S., 82, 1709 (1960) and U.S. Pat. Nos. 2,727,905 and 4,324,878.

The oxidation of the steroid A-ring by ozone ($O_3$) is known, see J.O.C. 23, 1787 (1958), U.S. Pat. No. 3,285,918 and European Patent Application 88300697.5 published Aug. 3, 1988 as European Publication Number 277,002 A2.

The oxidation of the steroid A-ring by $MnO_4^{-1}/IO_4^{-1}$ is known, see J. Med. Chem., 27, 1690 (1984) and European Patent Application 88300697.5 published Aug. 3, 1988 as European Publication Number 277,002 A2.

The oxidation of a steroidal $C_{17}$ enone side chain to the corresponding 17β—COOH by ozone has been reported, see J.A.C.S. 78, 1414 (1956). The cleavage of 1,3-dicarbonyls is known, see J.C.S. Chem. Comm., 1055 (1968). However, the oxidation of an alkoxyoxalkyl to give a carboxylic acid has not been reported.

The known methods of producing the 17β-carboxylic-3,5-secoandrostanes required that the particular $C_{17}$ side chain desired in the secosteroid (II) be present in the starting material to be oxidized or to a group which following oxidation of the steroid A-ring could readily be converted to the desired $C_{17}$ side chain, see, for example, European Patent Application 88300697.5 published Aug. 3, 1988 as European Publication Number 277,002 A2 on page 1167, lines 49–52. The process of the present invention differs from known methods because the one step process produces oxidation involving both ends of the steroid molecule in a simultaneous reaction. The use of glyoxylates as 1,3-dicarbonyls in an oxidation reaction is novel.

SUMMARY OF INVENTION

Disclosed is a process for the production of a 3,5-secoandrostan-5-one-3,17β-dioic acid of formula (II) where (A-I) $R_1$ is α-$R_{1\text{-}1}$:β-$R_{1\text{-}2}$ where one of $R_{1\text{-}1}$ and $R_{1\text{-}2}$ is —H and the other of $R_{1\text{-}1}$ and $R_{1\text{-}2}$ is —H, —F, —Cl, —Br, —I, —$OR_{1\text{-}3}$ where $R_{1\text{-}3}$ is —H or $C_1$-$C_6$ alkyl, —$SR_{1\text{-}3}$ where $R_{1\text{-}3}$ is as defined above, $R_2$ is —H:—H;

(A-II) $R_1$ is —H:—H, $R_2$ is α-$R_{2\text{-}1}$:β-$R_{2\text{-}2}$ where one of $R_{2\text{-}1}$ and $R_{2\text{-}2}$ is —H and the other of $R_{2\text{-}1}$ and $R_{2\text{-}2}$ is —H, —F, —Cl, —Br, —I, —$OR_{2\text{-}3}$ where $R_{2\text{-}3}$ is —H or $C_1$-$C_6$ alkyl, —$SR_{2\text{-}3}$ where $R_{2\text{-}3}$ is as defined above;

$R_7$ is α-$R_{7\text{-}1}$:β-$R_{7\text{-}2}$ where $R_{7\text{-}1}$ is —H, —F, —Cl, —Br, —I, —$OR_{7\text{-}3}$ where $R_{7\text{-}3}$ is —H or $C_1$-$C_6$ alkyl, and where $R_{7\text{-}2}$ is —H, —$CH_3$, —F, —Cl, —Br, —I, —$OR_{7\text{-}4}$ where $R_{7\text{-}4}$ is —H or $C_1$-$C_6$ alkyl, —$SR_{7\text{-}4}$ where $R_{7\text{-}4}$ is as defined above, with the proviso that one of $R_{7\text{-}1}$ and $R_{7\text{-}2}$ is —H;

(C-I) $R_{11}$ is α-H:β—O—, where β—O— is taken together with $R_9$ to form an epoxide between $C_9$ and $C_{11}$;

(C-II) $R_9$ is —H, —F or —Cl and $R_{11}$ is =O or α-H:β-$R_{11\text{-}1}$ where $R_{11\text{-}1}$ is —H or —OH;

$R_{16}$ is α-$R_{16\text{-}1}$:β-$R_{16\text{-}2}$ where one of $R_{16\text{-}1}$ and $R_{16\text{-}2}$ is —H and the other is —H, —OH and —$CH_3$ which comprises (1) contacting a 21-unsaturated progesterone of formula (I) where $R_1$, $R_2$, $R_7$, $R_9$, $R_{11}$ and $R_{16}$ are as defined above, and where $R_{22\text{-}1}$ is —H, —OH, $C_1$-$C_6$ alkyl, $C_4$-$C_7$ cycloalkyl, —φ optionally substituted with 1-5 —$NO_2$, —F, —Cl, —Br, —CN, $C_1$-$C_3$ alkyl, —$OR_{22\text{-}3}$ where $R_{22\text{-}3}$ is $C_1$-$C_3$ alkyl, —$NR_{22\text{-}4}R_{22\text{-}5}$ where $R_{22\text{-}4}$ and $R_{22\text{-}5}$ are the same or different and are selected from the group consisting of —H, $C_1$-$C_4$ alkyl and $C_4$-$C_7$ cycloalkyl, —O—$R_{22\text{-}6}$ where $R_{22\text{-}6}$ is $C_1$-$C_6$ alkyl, $C_4$-$C_7$ cycloalkyl and —φ; $R_{22\text{-}2}$ is —H, $C_1$-$C_6$ alkyl, $C_4$-$C_7$ cycloalkyl, —φ optionally substituted with 1-5 —$NO_2$, —F, —Cl, —Br, —CN, $C_1$-$C_3$ alkyl, —$OR_{22\text{-}7}$ where $R_{22\text{-}7}$ is $C_1$-$C_3$ alkyl, —$NR_{22\text{-}8}R_{22\text{-}9}$ where $R_{22\text{-}8}$ and $R_{22\text{-}9}$ are the same or different and are selected from the group consisting of —H, $C_1$-$C_4$ alkyl and $C_4$-$C_7$ cycloalkyl, —O—$R_{22\text{-}10}$ where $R_{22\text{-}10}$ is $C_1$-$C_6$ alkyl, $C_4$-$C_7$ cycloalkyl and —φ, —CO—O—$R_{22\text{-}11}$ where $R_{22\text{-}11}$ is $C_1$-$C_{10}$ alkyl, $C_4$-$C_7$ cycloalkyl or —φ optionally substituted with 1 thru 5 —$NO_2$, —F, —Cl, —Br, —CN, $C_1$-$C_3$ alkyl, —$OR_{22\text{-}12}$ where $R_{22\text{-}12}$ is $C_1$-$C_3$ alkyl, —$NR_{22\text{-}13}R_{22\text{-}14}$ where $R_{22\text{-}13}$ and $R_{22\text{-}14}$ are the same or different and are selected from the group consisting of —H, $C_1$-$C_4$ alkyl with $O_3$, (2) contacting the reaction mixture of step (1) with an aqueous hydroxide or a means for generating hydroxide and (3) neutralizing the hydroxide with an acid.

Also disclosed is a process for the production of a 3,5-secoandrostan-5-one-3,17β-dioic acid of formula (II) where $R_1$, $R_2$, $R_7$, $R_9$, $R_{11}$ and $R_{16}$ are as defined above which comprises, (1) contacting a 21-unsaturated progesterone of formula (I) where $R_1$, $R_2$, $R_7$, $R_9$, $R_{11}$, $R_{16}$, $R_{22\text{-}1}$ and $R_{22\text{-}2}$ are as defined above, with an oxidizing agent.

Further, disclosed are the 21-unsaturated progesterones (I-C) and 3,5-secoandrostan-5-one-3,17β-dioic acids (II-C) which include the 21-unsaturated progesterones (I) and 3,5-secoandrostan-5-one-3,17β-dioic acids (II) where the C-ring is an 9β,11β-epoxide.

DETAILED DESCRIPTION OF THE INVENTION

The 21-unsaturated progesterones (I) are known compounds, see U.S. Pat. Nos. 2,727,905 and 4,325,878 and J.A.C.S. 82, 1709 (1960). Alternatively they can readily be prepared from known substituted progesterones by methods known to those skilled in the art, see, for example, U.S. Pat. No. 2,727,905 and Gazz. Chim. Ital. 84, 312 (1954). In CHART A and the claims, the $C_{17}$ side chain is set forth as —CO—CH=C($R_{22\text{-}1}$)($R_{22\text{-}2}$) which when $R_{22\text{-}1}$ is —OH is, as is known to those skilled in the art, equivalent to —CH$_2$—CO—R$_{22\text{-}2}$. It is preferred that R$_{22\text{-}1}$ is —OH and R$_{22\text{-}2}$ is —CO—O—R$_{22\text{-}11}$. It is preferred that R$_{22\text{-}11}$ is C$_1$-C$_4$ alkyl, it is more preferred that R$_{22\text{-}11}$ is C$_1$ or C$_2$ alkyl.

There are two different ways to practice the process of the present invention. The first method involves contacting the 21-unsaturated progesterones (I), with O$_3$, followed by aqueous hydroxide, or a means for generating hydroxide, and then neutralizing the hydroxide with acid. The 21-unsaturated progesterones (I) need to be dissolved in an appropriate solvent or mixtures thereof. Suitable solvents include, methylene chloride, acetic acid, chloroform, methanol, ethanol, propanol, isopropanol, butanol, ethyl acetate, DMSO, acetone, dioxane, water and mixtures thereof depending on the particular 21-unsaturated progesterone (I). The preferred solvent is a methylene chloride/acetic acid mixture. The ozonolysis if operable in a temperature range of about 0° to about −100°, preferably about −20° to about −80°, more preferably about −78°. While it is operable to add aqueous hydroxide to the reaction mixture, it is preferred that the aqueous hydroxide be added in two steps. First, just water and then solid hydroxide. Means for generating hydroxide include, bicarbonate, carbonate or an amine. Amines, even those that are not very water soluble, generate hydroxide. They react with water, abstracting a proton from the water molecule generating an amine cation and hydroxide (anion). The reaction of the amines (A) and water can be visualized as A+H$_2$O - - - →A—H+ +OH−. Operable amines include, for example, diethylamine, triethylamine, pyridine, aniline, piperazine, pyrolidine, piperidine, morpholine, 1-methylpiperidine, α-naphthylamine, imidazole and substituted imidazoles, 1,2,4-triazole and substituted 1,2,4-triazoles, benzimidazole and substituted benzimidazoles, and equivalents thereof. For example, if the amine was triethylamine or pyridine, the cation generated would be (CH$_3$CH$_2$)$_3$NH+ and pyridinium respectively along with hydroxide. It is preferred the hydroxide be sodium or potassium hydroxide. It is desirable to warm the reaction mixture either before or after the addition of the aqueous base to prevent the reaction mixture from freezing as is known to those skilled in the art. It is preferred to warm the reaction mixture to about 0°.

When the 21-unsaturated progesterone (I) is contacted with O$_3$ the contacting is effectuated by bubbling/sparging O$_3$ gas thru a solution of the 21-unsaturated progesterone (I). While the reaction will proceed with less than 2 equivalents of O$_3$, it is preferred that at least 2 equivalents of O$_3$ be used since that amount is required for the reaction to go to completion. Any large excess is not harmful, just wasteful. As a practical matter the reaction mixture is contacted with somewhat greater than 2 equivalents. It is preferred to remove the excess O$_3$ from the reaction mixture prior to contacting with aqueous hydroxide. The O$_3$ is removed by sparging with oxygen, and then the oxygen is removed by sparging with an inert gas such as nitrogen. If the excess O$_3$ is removed, prior to contacting with the aqueous hydroxide, then it is preferred to contact the reaction mixture with H$_2$O$_2$ prior to contacting the reaction mixture with the aqueous hydroxide. Following the addition of the aqueous hydroxide, the excess hydroxide is neutralized by the addition of an acid. Since the only purpose of the acid is to neutralize the hydroxide virtually any moderately strong or strong acid is operable. Preferred acids are hydrochloric, sulfuric, phosphoric, nitric, acetic, perchloric, trifluoroacetic, citric, succinic, maleic, benzoic and p-TSA, more preferred are sulfuric and hydrochloric.

Using the second method, the 21-unsaturated progesterones (I) are dissolved in an appropriate solvent, as discussed above, and contacted with an oxidizing agent. The first type of oxidizing agent consists of an oxidant or means of generating the oxidant. The oxidant is selected from the group consisting of RuO$_4$, persulfate, pervanadate, pertungstate or MnO$_4^{-1}$. This oxidant can be used stoichiometrically, or preferably, it is used catalytically with a means for producing the oxidant, a reoxidant. Means for producing the oxidant include is selected from the group consisting of NaOCl, NaClO$_4$, IO$_4^{-1}$ and Ca(OCl)$_2$. Even catalytic amounts of the oxidant are operable provided 4 or more equivalents of the means for generating the oxidant (reoxidant) are present as is more fully discussed below.

Alternatively, the oxidizing agent is a two stage oxidant. With the two stage oxidants, it is believed the first oxidant oxidizes the 21-unsaturated progesterone (I) to a glycol and the second oxidant cleaves the glycol. The two stage oxidants include, for example, OsO$_4$/Pb(OAc)$_4$, KMnO$_4$/Pb(OAc)$_4$, OsO$_4$/IO$_4^{-1}$. The preferred two stage oxidants include osmium tetroxide followed by periodate or lead tetraacetate, and permanganate followed by periodate.

The oxidation reaction using the oxidizing agent is operable in a temperature range of about −100° to about 65°, preferably about −80° to about 40°. The reaction requires a total of 4 equivalents of the oxidizing agent. If catalytic amounts of the oxidant are used, then 4 equivalents of the reoxidant (such as IO$_4^{-1}$) are required. Alternatively, if 2 equivalents of the oxidant (for example, OsO$_4$) are used then 2 equivalents of the reoxidant (for example, IO$_4^{-1}$) are required. The reaction will proceed with less than 4 equivalents of the oxidizing agent but not to completion. It is therefore preferred that at least 4 equivalents of the oxidizing agent or a means for generating be used.

It is preferred that following the contacting of the 22-saturated progesterone (I) with the oxidizing agent, that aqueous hydroxide be added. While it is operable to add aqueous hydroxide to the reaction mixture, it is preferred that the aqueous hydroxide be added in two steps. First, just water and then solid hydroxide. Means for generating hydroxide include, bicarbonate, carbonate or an amine. It is preferred the base be sodium or potassium hydroxide. Following the addition of the aqueous hydroxide, the excess hydroxide is neutralized by the addition of an acid. Virtually any moderately strong or strong acid is operable. Preferred acids are hydrochloric, sulfuric, phosphoric, nitric, acetic, perchloric, trifluoroacetic, citric, succinic, maleic, benzoic and p-TSA. It is desirable to warm the reaction mixture either before or after the addition of the aqueous base to prevent the reaction mixture from freezing as is known to those skilled in the art. It is preferred to warm the reaction mixture to about 0°.

The final product, the seco-steroid (II) is extracted into a variety of organic solvents. Preferred is ethyl acetate or methylene chloride. If methylene chloride is used the seco-steroid (II) can be converted to the 4-aza steroids directly. If it is desired to crystallize the seco-steroid (II), it is preferred to use ethyl acetate for isolation.

The seco-steroid (II) is useful in producing $\Delta^5$-4-aza-17-carbonyl steroids (III) which are transformed to 5α-4-aza amides (IV), useful pharmaceuticals, all by means well known to those skilled in the art, see, for example, European Patent Application 88300697.5 published Aug. 3, 1988 as European Publication Number 272,002 A2, U.S. Pat. Nos. 4,325,878 and 4,377,584, J. Steroid Biochem., 19, 385 (1983), J. Med. Chem., 27, 1690 (1984). With the $\Delta^5$-4-aza-17-carbonyl steroids (III) $R_4$ is —H or $C_1$-$C_4$ and $R_{20}$ is —OH (acid), —$OR_{20\text{-}1}$ (esters) where $R_{20\text{-}1}$ is $C_1$-$C_4$ alkyl or —$\phi$, and —$NR_{20\text{-}2}R_{20\text{-}3}$ (amides) where $R_{20\text{-}2}$ and $R_{20\text{-}3}$ are the same or different and are —H or $C_1$-$C_3$ alkyl.

DEFINITIONS AND CONVENTIONS

The definitions and explanations below are for the terms as used throughout this entire document including both the specification and the claims.

I. Conventions for Formulas and Definitions of Variables

The chemical formulas representing various compounds or molecular fragments in the specification and claims may contain variable substituents in addition to expressly defined structural features. These variable substituents are identified by a letter or a letter followed by a numerical subscript, for example, "$Z_i$" or "$R_i$" where "i" is an integer. These variable substituents are either monovalent or bivalent, that is, they represent a group attached to the formula by one or two chemical bonds. For example, a group $Z_i$ would represent a bivalent variable if attached to the formula $CH_3$—C(=$Z_i$)H. Groups $R_i$ and $R_j$ would represent monovalent variable substituents if attached to the formula $CH_3$—$CH_2$—C(-$R_i$)($R_j$)$H_2$. When chemical formulas are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately preceding atom to the left which is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. Likewise the term "$R_6$" represents a variable substituent (either monovalent or bivalent) at the $C_6$ position.

Chemical formulas or portions thereof drawn in a linear fashion represent atoms in a linear chain. The symbol "—" in general represents a bond between two atoms in the chain. Thus $CH_3$—O—$CH_2$—CH($R_i$)—$CH_3$ represents a 2-substituted-1-methoxypropane compound. In a similar fashion, the symbol "=" represents a double bond, e.g., $CH_2$=C($R_i$)—O—$CH_3$, and the symbol "≡" represents a triple bond, e.g., HC≡C—CH($R_i$)—$CH_2$—$CH_3$. Carbonyl groups are represented in either one of two ways: —CO— or —C(=O)—, with the former being preferred for simplicity.

Chemical formulas of cyclic (ring) compounds or molecular fragments can be represented in a linear fashion. Thus, the compound 4-chloro-2-methylpyridine can be represented in linear fashion by $N^*$=C($CH_3$)—CH=CCl—CH=$C^*$H with the convention that the atoms marked with an asterisk (*) are bonded to each other resulting in the formation of a ring. Likewise, the cyclic molecular fragment, 4-(ethyl)-1-piperazinyl can be represented by —$N^*$—($CH_2$)$_2$—N($C_2H_5$)—$CH_2$—$C^*H_2$.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —C($S_1$)($X_2$)— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other. In chemical structural formulas depicting such compounds, a substituent ($X_1$) which is "below" another substituent ($X_2$) will be identified as being in the alpha ($\alpha$) configuration and is identified by a broken, dashed or dotted line attachment to the carbon atom, i.e., by the symbol " - - - " or " . . . ". The corresponding substituent attached "above" ($X_2$) the other ($X_1$) is identified as being in the beta ($\beta$) configuration and is indicated by an unbroken line attachment to the carbon atom.

When a variable substituent is bivalent, the valences may be taken together or separately or both in the definition of the variable. For example, a variable $R_i$ attached to a carbon atom as -C(=$R_i$)— might be bivalent and be defined as oxo or keto (thus forming a carbonyl group (—CO—) or as two separately attached monovalent variable substituents $\alpha$—$R_{i\text{-}j}$ and $\beta$—$R_{i\text{-}k}$. When a bivalent variable, $R_i$, is defined to consist of two monovalent variable substituents, the convention used to define the bivalent variable is of the form "$\alpha$—$R_{i\text{-}j}$:$\beta$—$R_{i\text{-}k}$" or some variant thereof. In such a case both $\alpha$—$R_{i\text{-}j}$ and $\beta$—$R_{i\text{-}k}$ are attached to the carbon atom to give —C($\alpha$—$R_{i\text{-}j}$)($\beta$—$R_{i\text{-}k}$)—. For example, when the bivalent variable $R_6$, —C(=$R_6$)— is defined to consist of two monovalent variable substituents, the two monovalent variable substituents are $\alpha$—$R_{6\text{-}1}$:$\beta$—$R_{6\text{-}2}$, . . . $\alpha$—$R_{6\text{-}9}$:$\beta$—$R_{6\text{-}10}$, etc, giving —C($\alpha$—$R_{6\text{-}1}$)($\beta$—$R_{6\text{-}2}$)—, . . . —C($\alpha$—$R_{6\text{-}9}$)($\beta$—$R_{6\text{-}10}$)—, etc. Likewise, for the bivalent variable $R_{11}$, —C(=$R_{11}$)—, two monovalent variable substituents are $\alpha$—$R_{11\text{-}1}$:$\beta$—$R_{11\text{-}2}$. For a ring substituent for which separate $\alpha$ and $\beta$ orientations do not exist (e.g. due to the presence of a carbon carbon double bond in the ring), and for a substituent bonded to a carbon atom which is not part of a ring the above convention is still used, but the $\alpha$ and $\beta$ designations are omitted.

Just as a bivalent variable may be defined as two separate monovalent variable substituents, two separate monovalent variable substituents may be defined to be taken together to form a bivalent variable. For example, in the formula —$C_1$($R_i$)H—$C_2$($R_j$)H— ($C_1$ and $C_2$ define arbitrarily a first and second carbon atom, respectively) $R_i$ and $R_j$ may be defined to be taken together to form (1) a second bond between $C_1$ and $C_2$ or (2) a bivalent group such as oxa (—O—) and the formula thereby describes an epoxide. When $R_i$ and $R_j$ are taken together to form a more complex entity, such as the group —X—Y—, then the orientation of the entity is such that $C_1$ in the above formula is bonded to X and $C_2$ is bonded to Y. Thus, by convention the designation " . . . $R_i$ and $R_j$ are taken together to form —$CH_2$—$CH_2$—O—CO— . . . " means a lactone in which the carbonyl is bonded to $C_2$. However, when designated "... $R_j$ and $R_i$ are taken together to form —CO—O—$CH_2$—$CH_2$— the convention means a lactone in which the carbonyl is bonded to $C_1$.

The carbon atom content of variable substituents is indicated in one of two ways. The first method uses a prefix to the entire name of the variable such as "$C_1$-$C_4$", where both "1" and "4" are integers representing the minimum and maximum number of carbon atoms in the variable. The prefix is separated from the variable by a space. For example, "$C_1$-$C_4$ alkyl" represents alkyl of 1 through 4 carbon atoms, (including isomeric forms thereof unless an express indication to the contrary is given). Whenever this single prefix is given, the prefix indicates the entire carbon atom content of the variable being defined. Thus $C_2$-$C_4$ alkoxycarbonyl describes a group $CH_3$—$(CH_2)_n$—O—CO— where n is zero, one or two. By the second method the carbon atom content of only each portion of the definition is indicated separately by enclosing the "$C_i$-$C_j$" designation in parentheses and placing it immediately (no intervening space) before the portion of the definition being defined. By this optional convention ($C_1$-$C_3$)alkoxycarbonyl has the same meaning as $C_2$-$C_4$ alkoxycarbonyl because the "$C_1$-$C_3$" refers only to the carbon atom content of the alkoxy group. Similarly while both $C_2$-$C_6$ alkoxyalkyl and ($C_1$-$C_3$)alkoxy(C $_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

II. Definitions

All temperatures are in degrees Centigrade.

$O_3$ refers to ozone.

Hydroxide refers to $OH^{-1}$ and when the term is used in the specification and claims it includes a means for generating hydroxide.

—φ refers to phenyl.

DMSO refers to dimethylsulfoxide.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, solubility, patient acceptance and bioavailability.

When solvent pairs are used, the ratios of solvents used are volume/volume (v/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

PREPARATION 1

21-Benzylidenepregn-4-ene-3,20-dione (I)

Progesterone 3-methyl enol ether is slurried in methanol (13 ml) and benzaldehyde (3.4 ml) is added. Sodium methoxide (25% wt/wt in methanol, 13 ml) is added, the mixture heated under reflux for 2 hr, and then cooled to 20°–25°. The pH is adjusted to 1 by the addition of hydrochloric acid (6N, 15 ml) and the mixture stirred at 30° for 2 hr. Water (30 ml) is added and the mixture filtered to give the title compound.

EXAMPLE 1

3,5-Secoandrost-5-one-3,17β-dioic acid (II)

21-oxalylpregn-4-ene-3,20-dione methyl ester [I, Gass. Chim. Ital., 84, 312 (1954), 20 g] is dissolved in methylene chloride (100 ml). Acetic acid (3.4 g) is added and the mixture is cooled to < −70°. Ozone is sparged through the mixture until excess ozone is present as indicated by a green color. Oxygen is then sparged until the excess ozone is removed and then nitrogen is sparged until the oxygen is removed. The mixture is then warmed to 0° and water (24 ml) is added. After the mixture warms to 20° hydrogen peroxide (30%, 5 ml) is added and the mixture stirred for 1 hr. Sodium hydroxide (10%, 50 ml) is added. The pH is adjusted by 2 by the addition of concentrated sulfuric acid (16 ml) and methylene chloride is added to dissolve the product. The organic mixture is washed with water (2×50 ml) and concentrated (about 40 ml). The solvent is exchanged to ethyl acetate (40 ml), the mixture cooled to 0° and the hepatane (100 ml) is added to crystallize the title compound, mp 197.3°–202.6°.

EXAMPLE 2

3,5-Secoandrost-5-one-3,17β-dioic acid (II)

21-Benzylidenepregn-4-ene-3,20-dione (I, PREPARATION 1, 20 g) is dissolved in methylene chloride (80 ml) and methanol (20 ml). The solution is cooled to −60° and ozone added until an excess is present as indicated by a light blue color. Water (10 ml) is added and the solution warmed to 20°–25°. The resulting solution is extracted with aqueous sodium hydroxide (5%, 100 ml). The aqueous solution is acidified to pH 2 by addition of hydrochloric acid (50%) and extracted with ethyl acetate (100 ml). The organic phase is dried over sodium sulfate and concentrated to 40 ml by distillation under reduced pressure. The mixture is cooled to 0° for one hr and the product collected by filtration to give the title compound, mp 203°–205°.

EXAMPLE 3

3,5-Secoandrost-5-3,17β-dioic acid (II)

A solution of 21-oxalylpregn-4-ene-3,20-dione methyl ester (I, 7.88 g) in methylene chloride (20 ml) and methanol (5 ml) is cooled to −40° and ozone added until an excess is present as indicated by the presence of a light blue color. Aqueous potassium carbonate (10%, 20 ml) is added and the mixture warmed to 20°–25°. The phases are separated and the aqueous phase acidified to pH 2 by addition of aqueous sulfuric acid (10%). The mixture is extracted with ethyl acetate (50 ml). The organic phase is concentrated to dryness to provide the title compound, mp 192°–208°.

EXAMPLE 4

3,5-Secoandrost-5pone-3,17β-dioic acid (II)

A solution of potassium carbonate (5.5 g in 25 ml of water) is added to a solution of 21-oxalylpregn-4-ene-3,20-dione methyl ester (I, 3.9 g) in t-butanol (100 ml). A solution of sodium metaperiodate (3.0 g in 20 ml of water) is prepared and 2 ml of this solution is added in one portion to the steroid solution. A solution of potassium permanganate (0.6 g in 30 ml of water) is prepared and 10 ml is added to the steroid solution. The reaction mixture is kept at 40° for 3 hr after the additions are complete the mixture is filtered through celite and enough sodium bisulfite added to discharge the pink color. The mixture is then concentrated to half volume under reduced pressure and extracted with ethyl acetate (50 ml). The organic phase is dried and concentrated to 10 ml volume and cooled. The product crystals are collected by filtration to give the title compound, 193°–201°.

EXAMPLE 5

3,5-Secoandrost-5-one-3,17β-dioic acid (II)

A solution of ruthenium tetroxide (RuO$_4$) is prepared by suspending ruthenium dioxide (RuO$_2$, 0.169 g) in acetone (10 ml) and adding a solution of sodium metaperiodate (2.5 g in 10 ml of water). A solution of 21-oxalylpregn-4-ene-3,20-dione methyl ester (I, 1.0 g) in acetone (10 ml) is added dropwise to the ruthenium tetroxide solution. As the solution changes color from yellow to black, a solution of sodium metaperiodate (2.5 g in 10 ml of water) is added to maintain the yellow color. After 4 hours the excess ruthenium tetroxide is is reacted by the addition of isopropanol. The mixture is filtered through celite and concentrated under reduced pressure to remove the acetone. The product is then extracted with ethyl acetate (20 ml). This solution is then dried over sodium sulfate and concentrated to dryness to give the title compound, mp 189°–203°.

CHART A

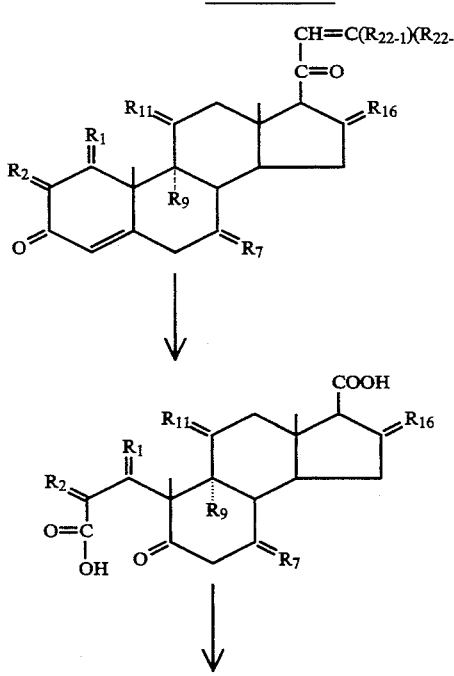

-continued
CHART A

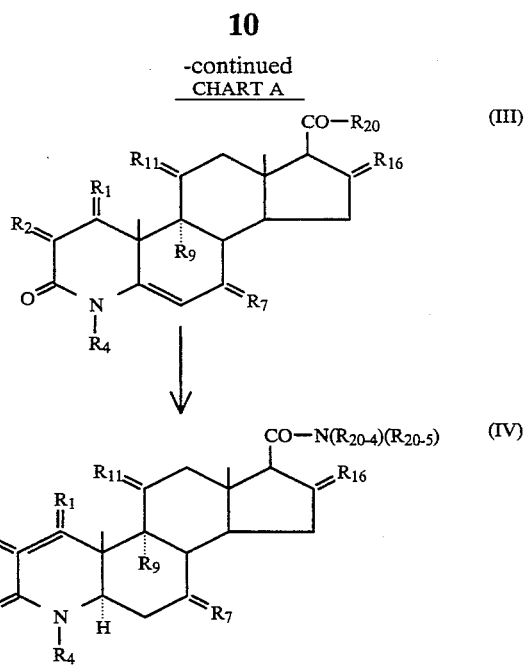

CHART B

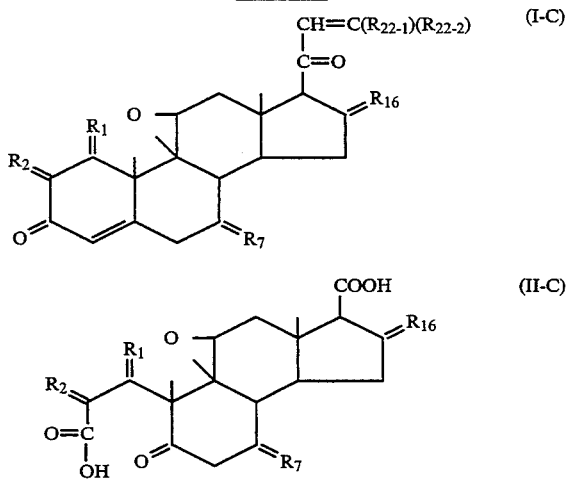

I claim:
1. A process for the production of a 3,5-secoandrostan-5-one-3,17β-dioic acid of formula (II)

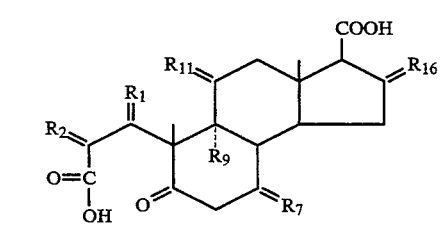

where
(A-I) $R_1$ is α—$R_{1-1}$:β—$R_{1-2}$ where one of $R_{1-1}$ and $R_{1-2}$ is —H and the other of $R_{1-1}$ and $R_{1-2}$ is —H, —F, —Cl, —Br, —I, —$OR_{1-3}$ where $R_{1-3}$ is —H or $C_1$-$C_6$ alkyl, —$SR_{1-3}$ where $R_{1-3}$ is as defined above, $R_2$ is —H:—H;
(A-II) $R_1$ is —H:—H, $R_2$ is α—$R_{2-1}$:β—$R_{2-2}$ where one of $R_{2-1}$ and $R_{2-2}$ is —H and the other of $R_{2-1}$ and $R_{2-2}$ is —H, —F, —Cl, —Br, —I, —$OR_{2-3}$ where $R_{2-3}$ is —H or $C_1$-$C_6$ alkyl, —$SR_{2-3}$ where $R_{2-3}$ is as defined above;

$R_7$ is α—$R_{7-1}$:β—$R_{7-2}$ where $R_{7-1}$ is —H, —F, —Cl, —Br, —I, —$OR_{7-3}$ where $R_{7-3}$ is —H or $C_1$-$C_6$ alkyl, and where $R_{7-2}$ is —H, —$CH_3$, —F, —Cl, —Br, —I, —$OR_{7-4}$ is —H or $C_1$-$C_6$ alkyl, —$SR_{7-4}$ where $R_{7-4}$ where $R_{7-4}$ is as defined above, with the proviso that one of $R_{7-1}$ and $R_{7-2}$ is —H;

(C-I) $R_{11}$ is α—H:β—O—, where β—O— is taken together with $R_9$ to form an epoxide between $C_9$ and $C_{11}$;

(C-II) $R_9$ is —H, —F or —Cl and $R_{11}$ is =O or α—H:β—$R_{11-1}$ where $R_{11-1}$ is —H or —OH;

$R_{16}$ is α—$R_{16-1}$:β—$R_{16-2}$ where one of $R_{16-1}$ and $R_{16-2}$ is —H and the other is —H, —OH and —$CH_3$ which comprises (1) contacting a 21-unsaturated progesterone of formula (I)

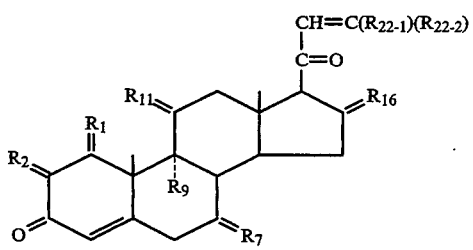

where $R_1$, $R_2$, $R_7$, $R_9$, $R_{11}$ and $R_{16}$ are as defined above, and where $R_{22-1}$ is

—OH,

—O—$R_{22-6}$ where $R_{22-6}$ is $C_1$-$C_6$ alkyl, $C_4$-$C_7$ cycloalkyl and —φ; $R_{22-2}$ is —H, $C_1$-$C_6$ alkyl, $C_4$-$C_7$ cycloalkyl, —φ optionally substituted with 1–5 —$NO_2$, —F, —Cl, —Br, —CN, $C_1$-$C_3$ alkyl, —$OR_{22-7}$ where $R_{22-7}$ is $C_1$-$C_3$ alkyl, —$NR_{22-8}R_{22-9}$ where $R_{22-8}$ and $R_{22-9}$ are the same or different and are selected from the group consisting of —H, $C_1$-$C_4$ alkyl and $C_4$-$C_7$ cycloalkyl, —O—$R_{22-10}$ where $R_{22-10}$ is $C_1$-$C_6$ alkyl, $C_4$-$C_7$ cycloalkyl and —φ, —CO—O—$R_{22-11}$ where $R_{22-11}$ is $C_1$-$C_{10}$ alkyl, $C_4$-$C_7$ cycloalkyl or —φ optionally substituted with 1 thru 5 —$NO_2$, —F, —Cl, —Br, —CN, $C_1$-$C_3$ alkyl, —$OR_{22-12}$ where $R_{22-12}$ is $C_1$-$C_3$ alkyl, —$NR_{22-13}R_{22-14}$ where $R_{22-13}$ and $R_{22-14}$ are the same or different and are selected from the group consisting of —H, $C_1$-$C_4$ alkyl with $O_3$ in the presence of less than 50% of a carboxylic acid, (2) contacting the reaction mixture of step (1) with an aqueous hydroxide or a means for generating hydroxide and (3) neutralizing the hydroxide with an acid.

2. A process for the production of a 3,5-secoandrostan-5-one-3,17β-dioic acid (II) according to claim 1 where $R_{22-1}$ is —OH and $R_{22-2}$ is —CO—O—$R_{22-11}$ where $R_{22-11}$ is $C_1$-$C_4$ alkyl.

3. A process for the production of a 3,5-secoandrostan-5-one-3,17β-dioic acid (II) according to claim 1 where the aqueous hydroxide is added in two steps, first water followed by the hydroxide.

4. A process for the production of a 3,5-secoandrostan-5-one-3,17β-dioic acid (II) according to claim 1 where the hydroxide is generated from bicarbonate, carbonate or an amine.

5. A process for the production of a 3,5-secoandrostan-5-one-3,17β-dioic acid (II) according to claim 1 where any excess $O_3$ is removed prior to addition of the aqueous hydroxide.

6. A process for the production of a 3,5-secoandrostan-5-one-3,17β-dioic acid (II) according to claim 5 where $H_2O_2$ is added following removal of the excess $O_3$ and prior to contacting with aqueous hydroxide.

7. A process for the production of a 3,5-secoandrostan-5-one-3,17β-dioic acid (II) according to claim 1 where the reaction mixture is warmed before the addition of the aqueous hydroxide.

8. A process for the production of a 3,5-secoandrostan-5-one-3,17β-dioic acid (II) according to claim 1 where the reaction mixture is warmed after the addition of the aqueous hydroxide.

9. A process for the production of a 3,5-secoandrostan-5-one-3,17β-dioic acid (II) according to claim 1 where at least 2 equivalents of $O_3$ are used.

10. A process for the production of a 3,5-secoandrostan-5-one-3,17β-dioic acid (II) according to claim 1 where the acid is selected from the group consisting of hydrochloric, sulfuric, phosphoric, nitric, acetic, perchloric, trifluoroacetic, citric, succinic, maleic, benzoic and p-TSA.

11. A 3,5-secoandrostan-5-one-3,17β-dioic acid of formula (II-C)

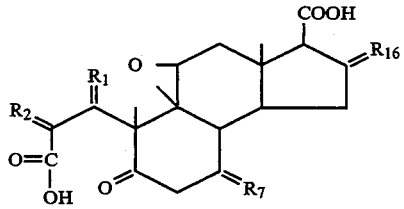

where (A-I) $R_1$ is α—$R_{1-1}$:β—$R_{1-2}$ where one of $R_{1-1}$ and $R_{1-2}$ is —H and the other of $R_{1-1}$ and $R_{1-2}$ is —H, —F, —Cl, —Br, —I, —$OR_{1-3}$ where $R_{1-3}$ is —H or $C_1$-$C_6$ alkyl, —$SR_{1-3}$ where $R_{1-3}$ is as defined above, $R_2$ is —H:—H;

(A-II) $R_1$ is —H:—H, $R_2$ is α—$R_{2-1}$:β—$R_{2-2}$ where one of $R_{2-1}$ and $R_{2-2}$ is —H and the other of $R_{2-1}$ and $R_{2-2}$ is —H, —F, —Cl, —Br, —I, —$OR_{2-3}$ where $R_{2-3}$ is —H or $C_1$-$C_6$ alkyl, —$SR_{2-3}$ where $R_{2-3}$ is as defined above;

$R_7$ is α—$R_{7-1}$:β—$R_{7-2}$ where $R_{7-1}$ is —H, —F, —Cl, —Br, —I, —$OR_{7-3}$ where $R_{7-3}$ is —H or $C_1$-$C_6$ alkyl, and where $R_{7-2}$ is —H, —$CH_3$, —F, —Cl, —Br, —I, —$OR_{7-4}$ where $R_{7-4}$ is —H or $C_1$-$C_6$ alkyl, —$SR_{7-4}$ where $R_{7-4}$ is as defined above, with the proviso that one of $R_{7-1}$ and $R_{7-2}$ is —H;

$R_{16}$ is α—$R_{16-1}$:β—$R_{16-2}$ where one of $R_{16-1}$ and $R_{16-2}$ is —H and the other is —H, —OH and —$CH_3$.

* * * * *